United States Patent [19]

Rozzell

[11] Patent Number: 4,921,796

[45] Date of Patent: May 1, 1990

[54] IMMOBILIZED CYCLODEXTRIN GLUCOSYLTRANSFERASE COMPOSITION FOR THE PRODUCTION OF CYCLODEXTRINS

[75] Inventor: J. David Rozzell, Cambridge, Mass.

[73] Assignee: Genetics Institute, Inc., Cambridge, Mass.

[21] Appl. No.: 183,193

[22] Filed: Apr. 19, 1988

[51] Int. Cl.$^5$ .................. C12P 19/18; C12N 9/10
[52] U.S. Cl. ............................ 435/97; 435/96; 435/193; 536/103
[58] Field of Search .................. 435/97, 96, 193; 536/103

[56] References Cited

U.S. PATENT DOCUMENTS

| | | | |
|---|---|---|---|
| 3,988,206 | 10/1976 | Shiosaka | 435/97 |
| 4,317,881 | 3/1982 | Yagi et al. | 435/97 |
| 4,384,898 | 5/1983 | Kada et al. | 435/97 |
| 4,418,144 | 11/1983 | Okada et al. | 435/97 |
| 4,477,568 | 10/1984 | Hokse et al. | 435/97 |
| 4,593,004 | 6/1986 | Boross et al. | 435/181 |
| 4,746,734 | 5/1988 | Tsuchiyama et al. | 536/103 |
| 4,781,977 | 11/1988 | Yagi et al. | 536/103 |
| 4,835,105 | 5/1989 | Seres et al. | 435/97 |
| 4,859,590 | 8/1989 | Thiem et al. | 435/97 |

*Primary Examiner*—Herbert J. Lilling
*Attorney, Agent, or Firm*—David L. Berstein; Bruce M. Eisen

[57] ABSTRACT

This invention relates to a method for the production of a composition comprising the enzyme cyclodextrin glucosyltransferase bound by covalent means to a support material in the presence of a source of divalent calcium ion, said immobilized cyclodextrin glucosyltransferase having a higher activity and greater stability than heretofore reported. This invention further relates to the use of the immobilized cyclodextrin glucosyltransferase for the production of cyclodextrins.

1 Claim, No Drawings

IMMOBILIZED CYCLODEXTRIN GLUCOSYLTRANSFERASE COMPOSITION FOR THE PRODUCTION OF CYCLODEXTRINS

This invention relates to a method for the production of a composition comprising the enzyme cyclodextrin glucosyltransferase bound by covalent means to a support material in the presence of a source of divalent calcium ion, said immobilized cyclodextrin glucosyltransferase having a higher activity and greater stability than heretofore reported. This invention further relates to the use of the immobilized cyclodextrin glucosyltransferase for the production of cyclodextrins.

BACKGROUND

The enzyme cyclodextrin glucosyl transferase (CGTase; E.C 2.4.1.19) has been identified in a limited group of bacteria, and catalyzes the partial conversion of starch, amylose, starch and amylose derivatives, glycogen, partially hydrolyzed starch, or maltooligosaccharides to cyclic oligosaccharides known as cyclodextrins The three most common forms of cyclodextrins are designated as alpha, beta, and gamma, being molecular rings containing 6, 7, and 8 glucopyranose units respectively Cyclodextrins find application as encapsulating agents and as additives for improving the handling and the functional properties of food, agricultural, and pharmaceutical products.

Cyclodextrin glucosyltransferase has been used almost exclusively in batch reactions. Very little information has been published about the preparation and use of cyclodextrin glucosyltransferases in immobilized form. Nakamura and Horikoshi describe in *Biotech. and Bioeng.* 19, 87–99 (1977) the adsorption of CGTase, chemically modified by succinylation, on a vinylpyridine copolymer. The enzyme is bound solely through ionic forces, and has the disadvantage of being gradually desorbed from the support during continuous operation. Kato and Horikoshi describe in *Biotech. and Bioeng.* 26, 595–598 (1984) the adsorption of a native CGTase to DIAION HP-20 resin; however, the authors report that only about 11% of the initial enzymatic activity was retained as a result of the immobilization, and as in the previous example, the enzyme desorbed from the resin during continuous operation. Ivony et al [*Journal of Applied Biochemistry* 5, 158–164 (1983)] and Boross et al (U.S. Pat. No. 4,593,004) describe a method for the covalent attachment of CGTase to a support using carbodiimide chemistry. This method prevents the leakage of CGTase from the support. However, the reported retention of activity as a result of the immobilization was only 3.4–6.3%; in addition, carbodiimide reagents can give rise to deleterious chemical modifications of enzymes and are relatively expensive coupling agents for use in an industrial process. Furthermore, the measured thermal stability of the CGTase immobilized by this method was low, showing a half-life of only about 63 minutes at 50° C. Clearly, methods for producing an immobilized CGTase enzyme which does not desorb, is stable to operational conditions, and has a high catalytic activity after immobilization are desired

DETAILED DESCRIPTION OF THE INVENTION

The present invention describes a method for producing a stable, long-lasting, and highly active CGTase immobilized to a support through covalent means. Numerous techniques for the immobilization of enzymes have been reported. However, certain of the known techniques are not particularly suitable for the immobilization of CGTases. For example, the adsorption methods described in *Biotech. and Bioeng.* 19, 87–99 (1977) and *Biotech. and Bioeng.* 26, 595–598 (1984) give rise to an immobilized enzyme which gradually desorbs during continuous operation, causing a loss of enzyme activity from the support and contamination of the product stream with protein leached from the support. The coupling of CGTase to supports bearing either pendant amine or pendant carboxyl groups through the action of carbodiimide reagents results in the loss of substantial amounts of the catalytic activity of the enzyme [Ivony et al, *Journal of Applied Biochemistry* 5, 158–164 (1983) and Boross et al, U.S. Pat. No. 4,593,004]. In none of the above-mentioned cases was the immobilized CGTase of high catalytic activity; the best example (Kato and Horikoshi) provided a reported productivity of about 10 grams of cyclodextrin produced per liter of bed volume per hour.

As an object of the present invention, it has been found that contacting a solution of CGTase with a support bearing pendant aldehyde functional groups in the presence of a source of divalent calcium ion at a concentration of 1 mM or higher produces a covalently immobilized CGTase which is stable and has a relatively high catalytic activity as compared to prior methods. In terms of stability, the immobilized CGtases prepared according to the method of the present invention have been found to display half-lives toward operational conditions of at least 1–2 months. No leaching of the CGTase from the support has been detected. In terms of catalytic activity, productivities of up to several grams of cyclodextrin produced per kg of immobilized biocatalyst per hour have been observed, which is approximately two orders of magnitude higher than previously reported.

As support materials, any of the materials known in the art which have, or may be modified so as to have, a pendant aldehyde functional group may be used in the practice of this invention. Examples of suitable support materials include polyacrolein; copolymers containing acrolein; polyglutaraldehyde and copolymers containing glutaraldehyde; aminoalkylated supports such as silica, alumina, titania, carbon, activated charcoal, diatomaceous earth, cellulose, and the like which have been treated with 3-aminopropyltriethoxy silane, a polyamine, or similar chemical so as to generate an accessible amine functionality on the surface of the support, followed by activation with a dialdehyde such as glutaraldehyde or xylopentadialdo-1,4-furanose; gelatin or chitosan which has been similarly treated with a dialdehyde; inorganic or organic materials treated consecutively with titanium tetrachloride, a diamine, and a dialdehyde according to the methods of Kennedy et al [*Enzyme and Microbial Technology*, 6, 68–72 (1984); *Enzyme and Microbial Technology*, 6, 228–232 (1984); *Applied Microbiology and Biotechnology*, 23, 157–162 (1986)] which are hereby incorporated by reference; aminoalkyl sepharose agarose, and the like which have been treated with a dialdehyde; cellulose and cellulose derivatives, sepharose, dextran, or similar carbohydrates which have been oxidized so as to generate accessible aldehyde functional groups, e.g. with periodate; starch or starch derivatives which have been oxidized with periodate; and other similar materials.

In accord with the practice of this invention, the CGTase enzyme to be immobilized may be isolated from any strain capable of producing the enzyme. Enzyme from at least five different strains has been tested to demonstrate the generality of the method, including CGTases produced from wild-type microorganisms, from mutated microorganisms, and from recombinant microorganisms. The CGTase may also be from either a mesophilic or a thermophilic microorganism, or alternatively, an enzyme having a genetically modified structure Thus, the source of the CGTase is not critical to the successful practice of the invention, and any enzyme having CGTase activity may be used. Some specific examples of microorganisms producing CGTases useful in the practice of this invention are *Bacillus macerans, Bacillus circulans, Bacillus meqaterium, Bacillus stearothermophilus, Bacillus ohbensis sp., Bacillus sp., Bacillus sp.* No. 38-2 (ATCC 21783), *Klebsiella pneumoniae* M5, *Micrococcus sp.* (ATCC 31606 and ATCC 31607), *Bacillus licheniformis,* or the product of cloned genes from any of these microorganisms.

Similarly, any method of isolation which allows the enzyme to be recovered without the loss of significant amounts of its catalytic activity may be used in the practice of the invention; enzyme in the form of filtered growth media, crude extracts, partially purified protein, or purified homogeneous protein has been immobilized using the method of this invention. The immobilization is preferably carried out at a pH of between about 4.0 and about 10.5; more preferably, the enzyme solution has a pH of from about 4.8 to about 9.0. The immobilization reaction may be carried out using only water as the solvent, or any of the known buffers capable of functioning in this pH range may be employed. Some examples of buffers useful for the immobilization of CGTase in the practice of this invention are sodium borate, potassium borate, sodium acetate, potassium acetate, sodium arsenate, potassium arsenate, 3-N-morphilinopropanesulfonic acid (MOPS), N-trishydroxymethyl-2-aminoethanesulfonic acid (TES), 2-N-morphilinoethanesulfonic acid (MES), HEPES, PIPES, and the like. The CGTase solution may be dialyzed against water or an aqueous buffer having the desired pH prior to carrying out the immobilization, if desired.

The temperature at which the immobilization is carried out may be varied according to convenience in the practice of this invention. Preferably, the temperature for the immobilization reaction is in the range of from about 4° C. to about 70° C.; most preferably, the temperature at which the immobilization is carried out is in the range of from about 10° C. to about 45° C. Similarly, the temperature of operation of the immobilized enzyme may be varied according to the optimum for activity and stability of the particular enzyme being used. Typical temperatures of use for the immobilized CGTases in the practice of this invention are in the range of about 4° C. to about 90° C.; most preferably, the temperature of use is in the range of from about 20° C. to about 75° C.

Critical to the success of the immobilization process is the presence of a source of divalent calcium ion in the CGTase solution. The source of the calcium ion may be selected according to convenience and cost. Some examples of divalent calcium sources useful in the practice of this invention are $CaCl_2$, $CaSO_4$, $CaCO_3$, and the like. The concentration of $Ca++$ in the immobilization reaction mixture should be at least 1 mM, and is preferably in the range of about 1 mM to about 25 mM.

The process for immobilizing CGTases thus comprises the following steps:
(1) Preparing a solution of CGTase containing a source of divalent calcium ion at a concentration of 1 mM or higher;
(2) Contacting the CGTase solution containing divalent calcium ion with a support bearing pendant aldehyde groups under conditions whereby at least a portion of the CGTase enzyme is bound to the support;
and optionally, (3) Washing the support-bound enzyme with a solution of high ionic strength containing divalent calcium ion so as to remove enzyme which has been adsorbed but not covalently bound;
(4) Recovering the support-bound enzyme from any remaining unbound enzyme.

The immobilized CGTase obtained by the procedure just described may also be further modified, if desired, to impart desirable characteristics to the immobilized CGTase composition. For example, the support-bound enzyme produced by coupling to pendant aldehdyes may be treated with a reducing agent such as sodium borohydride and the like to reduce any unreacted aldehydes and to further stabilize the linkage of the enzyme to the support. Alternatively, unreacted pendant aldehyde groups may be quenched with an amine-containing reagent such as glycine, ethanolamine, Tris, and other similar reagents.

The immobilized CGTase may be used immediately after preparation, or stored at refrigerator temperatures until ready for use.

The invention will now be described by the following examples, which are intended for illustrative purposes only, and are not intended to limit the scope of the invention.

EXAMPLES

Example 1: Immobilization of *Bacillus macerans* CGTase

A support matrix (0.8 grams) composed of silica dispersed in polyvinylchloride which had been pre-treated with polyethyleneimine (Amerace Corporation, Hackettstown, N.J. U.S.A.) was washed with 100 ml of 50 mM sodium phosphate buffer (standard buffer), pH 7.0, followed by treatment with 25 ml of 5% w/v glutaraldehyde solution, pH 7, in standard buffer. After 1 hour at 25° C., the glutaraldehyde activated support was flushed with 500 ml of 25 mM MOPS buffer (Sigma Chemical Company, St. Louis, Mo. U.S.A.), pH 7.0 (standard MOPS buffer). Calcium chloride was added to a final concentration of 5 mM to fifteen milliliters of an enzyme solution containing CGTase from *Bacillus macerans* (ATCC 8514), 4 mg/ml, in standard MOPS buffer, and this enzyme solution was recirculated through the support matrix for 90 minutes at a temperature of 25° C. The immobilized enzyme was then washed with standard MOPS buffer containing 5 mM $CaCl_2$ and 300 mM NaCl.

A protein balance showed that 22 mg of protein was immobilized covalently to the matrix. The biocatalyst was assayed by recirculating a solution of 63 ml of 2% w/v corn maltodextrin, DE 5, (A. E. Staley Manufacturing Co., Decatur, Ill. U.S.A.) containing 5 mM calcium chloride at 45° C. The amount of cyclodextrins produced were measured by HPLC using a cyclodextrin assay column purchased from Advanced Separation Technologies (N.J. U.S.A.). After 440 minutes, 41% of the maltodextrin was converted to cyclodextrins.

Example 2: Alternative Immobilization of CGTase

CGTase from *Bacillus macerans* was immobilized according to the procedure in Example 1 except that less protein was offered to the support matrix in the immobilization step (12.5 ml, 2.8 mg/ml). A protein balance showed that 10 mg of protein was bound to the support.

The immobilized enzyme was assayed in the same manner as in Example 1 at a temperature of 37° C. After 460 minutes, 42% of the maltodextrin substrate had been converted into cyclodextrins.

Example 3: Stability of the Immobilized CGTase

CGTase immobilized according to Example 1 was operated continuously at a temperature of 37° C. for the conversion of maltodextrin substrate solutions to cyclodextrins. Using a 2% maltodextrin substrate, the immobilized CGTase had lost 20% of its activity after 42 days of continuous operation; using a 4% maltodextrin substrate, the immobilized CGTase showed no loss in activity after 40 days; using an 8% maltodextrin substrate, the immobilized CGTase lost less than 10% of its activity after 25 days of continuous operation.

When the immobilized CGTase of Example 1 was operated continuously at a temperature of 45° C. for the conversion of 2% maltodextrin to cyclodextrin, the measured half-life of the biocatalyst was 45 days.

The stability of the immobilized CGTase enzyme of Example 2 in the continuous production of cyclodextrins was also measured. After 48 hours of continuous operation at 55° C., there was no detectable loss in enzymatic activity for the conversion of maltodextrins to cyclodextrins.

Example 4: Immobilization of CGTase on Porous Silica

One hundred grams of Aminopropyl Silica (Corning) was suspended in 250 ml of a 5% w/v solution of glutaraldehyde in 50 mM potassium phosphate buffer, pH 7.0. After 60 minutes at 25° C., the activated silica particles were collected by filtration and washed with buffer until no glutaraldehyde could be detected in the washings by a test with 2,4-dinitrophenylhydrazine. The support was then suspended in an aqueous solution containing 5 grams of CGTase from *Bacillus macerans* and calcium chloride added to a final concentration of 10 mM. The pH was adjusted to 6.8, and the immobilization was allowed to proceed for 2 hours on a rotary shaker. The immobilized enzyme was collected by filtration and washed with water containing calcium chloride (10 mM) and potassium chloride (500 mM). The immobilized CGTase was stored damp at refrigerator temperature until ready for use.

Example 5: Immobilization of CGTase on Chitosan

Chitosan particles (one gram) produced by dripping an aqueous solution of chitosan acetate into a bath of pH 10, are suspended in 5 ml of a solution of glutaraldehyde (5% w/v) in 25 mM potassium phosphate buffer, pH 7.0. After 60 minutes at room temperature, the activated chitosan particles are washed with 100 ml of buffer, and then the support is resuspended in 10 ml of 25 mM MOPS buffer, pH 7.0, containing 5 mM calcium chloride (standard MOPS buffer) and 60 mg of CGTase from *Bacillus macerans*. The immobilization reaction was allowed to proceed for 60 minutes, after which time the support bound CGTase was washed with 500 mM potassium chloride in MOPS buffer, followed by standard MOPS buffer. The immobilized CGTase was stored at refrigerator temperatures until ready for use.

Example 6: Immobilization of CGTase on Diatomaceous Earth

Diatomaceous earth (-24-48 mesh, Johns-Manville) is washed with deionized water, and the fines are decanted. To 100 ml of wet diatomaceous earth is added 500 ml of polyethyleneimine solution (Union Carbide, 5% w/v), and the mixture is shaken gently for 4 hours. The treated diatomaceous earth is collected by filtration, and washed exhaustively with water, followed by 50 mM potassium phosphate buffer, pH 7.0. The support is resuspended in 500 ml of glutaraldehyde in 50 mM potassium phosphate buffer (5% w/v) and mixed on a rotary shaker for 90 minutes, at the end of which time the support is collected by filtration and washed exhaustively with water. The activated diatomaceous earth support is then suspended in 500 ml of a 25 mM MOPS buffer solution containing 5 grams of CGTase (*Bacillus macerans*, Amano), 10 mM calcium sulfate, pH 7, and the immobilization reaction is allowed to proceed for 2 hours. The support is washed with 25 mM MOPS buffer containing 10 mM calcium sulfate and 500 mM potassium chloride and stored wet at 4° C. until ready for use.

Example 7: Immobilization of CGTase on Porous Alumina

CGTase from *Bacillus macerans* was immobilized on a polyethyleneimine-treated, glutaraldehyde activated porous alumina support obtained from UOP (Des Plaines, Ill. U.S.A.). The support material is suspended in 25 mM MOPS buffer containing 10 mM $CaCl_2$ and allowed to equilibrate for 1 hour prior to use. The immobilization was carried out at 25° C. in a 25 mM MOPS buffer containing 5 mM calcium chloride using 100 mg of CGTase per gram of support material. After a period of 2 hours, the immobilized enzyme is recovered by filtration and washed with water containing 0.5M potassium chloride and 10 mM $CaCl_2$, pH 6.5-7.0. The immobilized CGTase is stored damp at 4° C. until ready for use.

Example 8: Immobilization of CGTase on Aminoethyl Agarose

To five grams of aminoethyl agarose (Sigma Biochemical, St. Louis, Mo. U.S.A.) is added 50 ml of 25 mM potassium phosphate buffer, pH 7.0, containing glutaraldehyde (5% w/v), and the mixture is mixed on a rotary shaker for 2 hours The activated support is collected by filtration and washed exhaustively with 25 mM MES buffer, pH 7.0, containing 5 mM $CaCl_2$. The support is resuspended in 50 ml of 25 mM MES buffer, pH 7.5, containing 5 mM $CaCl_2$ and 0.5 grams of CGTase from *Bacillus macerans* (Enzyme Biosystems, Englewood Cliffs, N.J. U.S.A.). The immobilization reaction is allowed to proceed for 2 hours, after which time the support bound enzyme is washed with immobilization buffer containing 400 mM potassium chloride, followed by immobilization buffer. The immobilized CGTase is stored damp at 4° C. until ready for use.

Example 9: Immobilization of CGTase on Periodate-Oxidized Cellulose

Cellulose (60 grams) is suspended in 1000 ml of 0.25M sodium periodate solution at pH 3.6 with constant agitation and left in the dark for 3 hours at 20° C. At the end of this time the oxidized cellulose is recovered by filtration and washed with copious amounts of water. The cellulose is then suspended in 500 ml of a solution containing CGTase from *Bacillus macerans* (2.5 grams), calcium chloride (5 mM), pH 7.0, and the immobilization reaction is allowed to proceed for 4 hours with gentle agitation. Sodium borohydride (0.5 grams) is added and stirring continued for an additional 30 minutes, after which time the support bound enzyme is collected by filtration and washed consecutively with 0.5M NaCl and 5 mM $CaCl_2$, pH 7.0. The immobilized CGTase is stored in a damp state at 4° C.

Example 10: Production of Cyclodextrins in the Presence of Buffer

Immobilized CGTase prepared according to Example 1 was used for the continuous production of cyclodextrins from 2% maltodextrin (DE 5) as substrate. The pH of the solution was maintained at 7.0 using a 25 mM imidazole buffer. At a flow rate of 2.0 ml/min and 37° C., approximately 20% of the maltodextrin was continuously converted into cyclodextrins. The productivity of the biocatalyst sample was 0.58 grams cyclodextrin produced per gram of biocatalyst per hour.

Example 11: Production of Cyclodextrins at Alkaline pH

The procedure of Example 10 was repeated except that the buffer used was 25 mM sodium borate and the pH was maintained at 9.0. A protein balance showed that 15 mg of enzyme was bound. When assayed using a 2% maltodextrin substrate at 25° C., the productivity of the immobilized biocatalyst was 0.31 grams cyclodextrin produced per gram of biocatalyst per hour.

Example 12: Production of Cyclodextrin From Starch

The procedure of Example 1 was repeated except that 2% soluble potato starch was used as the substrate. The potato starch was autoclaved for 20 minutes at pH 2.5, and the pH was then adjusted to 4.3 with sodium acetate.

The potato starch solution was recirculated through the immobilized CGTase biocatalyst at a constant flow rate of 4 ml/minute and 50° C. After 10 minutes, 18% of the starch had been converted to cyclodextrins as measured by HPLC. The productivity of the biocatalyst was 1.4 grams of cyclodextrins produced per gram of biocatalyst per hour. The maximum conversion observed in this experiment was approximately 45%.

Example 13: Immobilization of CGtase From A Novel Bacillus sp.

Crude CGTase isolated by lyophilization of the fermentation broth of Bacillus sp. (ATCC 53605) was immobilized according to the procedure described in Example 1. Eleven mg of enzyme was bound to the support. Assay of the enzyme showed that approximately 25% of its catalytic activity was retained after immobilization. After 460 minutes of recirculation of 2% maltodextrin substrate, 26% conversion to cyclodextrins was observed. After 48 hours of continuous operation in the production of cyclodextrins at 55° C., no loss in activity could be observed.

Example 14: Immobilization of CGTase From a Novel Bacillus licheniformis

Fifty milliliters of a solution of crude CGTase isolated from *Bacillus licheniformis* (ATCC 53603), 0.6 mg protein /ml, was immobilized according to the procedure in Example 1. A protein balance showed that 19 mg of enzyme was immobilized (63%). Assay according to the procedure in Example 6 showed the conversion of 11% of maltodextrin substrate to cyclodextrins after 30 hours.

Example 15: Immobilization of Purified CGTase From An Alkalophilic Bacillus

Purified CGTase from an alkalophilic Bacillus (Alko; Rajamaki, Finland) was immobilized according to the procedure in Example 1. A protein balance showed that 13 mg of protein had been immobilized. The immobilized catalyst was used for the continuous conversion of 2% maltodextrin to cyclodextrins at 25° C. The productivity of the biocatalyst was 5.5 g/g-hr with a constant conversion of 50%. The biocatalyst showed no loss in activity over a 144 hour period at 37° C.

Example 16: Immobilization of Partially Purified CGTase From Bacillus macerans CGTase from *Bacillus macerans* (Amano; Troy, Va. U.S.A.), purified 10-fold over the preparation used in Example 1, was immobilized according to the procedure of Example 1. The amount of enzyme offered in the immobilization was 16.5 mg per gram of support, of which 100% was bound. The immobilized enzyme was assayed as in Example 9 using a 25 mM sodium borate buffer containing 5 mM calcium chloride At a constant level of 40% conversion, the productivity of the immobilized biocatalyst was 890 grams of cyclodextrin produced per kilogram biocatalyst per hour.

Example 17: Immobilization of Purified CGTase From Bacillus macerans

Purified CGTase from *Bacillus macerans* obtained from Chinoin Pharmaceutical and Chemical Works, Budapest, Hungary (30 mg) was immobilized according to the procedure in Example 15. Assay of the immobilized enzyme showed in a continuous manner showed a productivity of 3.2 grams of cyclodextrin produced from 2% maltodextrin as substrate per gram of biocatalyst per hour. The immobilized CGTase was capable of converting approximately 50% of maltodextrins or approximately 55% of soluble potato starch to cyclodextrins in a continuous manner.

Example 18: Immobilization of CGTase produced in a Recombinant Microorganism The gene encoding the CGTase from Bacillus so. ATCC 21783 was cloned into *E. coli* by the methods described in Maniatis, Fritsch, and Sambrook [*Molecular Clonino: A Laboratorv Manual*, Cold Spring Harbor Laboratory (1982)] and the references therein, which is hereby incorporated by reference. E. coli transformants containing the gene on an ampicillin resistant plasmid vector were grown under aerobic conditions at 37° C. After 24 hours, the supernatant was recovered by centrifugation and shown by assay to contain CGTase activity. The supernatant solution was immobilized by the procedure of Example 1, and the immobilized biocatalyst was assayed using 2% maltodextrin, DE 5, as the substrate. Using a peristaltic pump, the maltodextrin solution was recirculated through the immobilized recombinant CGTase biocatalyst at a flow rate of 0.4 ml/min. Approximately 50% of the maltodextrin was converted to cyclodextrins.

What is claimed is:

1. A method for the production of cyclodextrins which comprises contacting
   (a) an immobilized cyclodextrin glucosyltransferase composition prepared by contacting a solution containing an enzyme having cyclodextrin glucosyltransferase (CGTase) activity with a support bearing pendant aldehyde groups in the presence of a source of divalent calcium ion at a concentration of at least 1 mM under conditions such that at least a portion of the enzyme is bound covalently to the support with
   (b) a solution containing starch, amylose, glycogen, degraded or partially degraded starch or starch derivatives, or maltodextrins.

* * * * *